United States Patent [19]

Jenkner

[11] 4,036,894

[45] July 19, 1977

[54] PROCESS FOR PRODUCING HALOGENATED 2,2-BIS-(4-HYDROXYPHENYL)-PROPANE

[75] Inventor: Herbert Jenkner, Cologne, Germany

[73] Assignee: Chemische Fabrik Kalk GmbH, Germany

[21] Appl. No.: 667,292

[22] Filed: Mar. 16, 1976

[30] Foreign Application Priority Data

Mar. 19, 1975 Germany .............................. 2511981

[51] Int. Cl.$^2$ .................... C07C 39/24; C07C 39/16
[52] U.S. Cl. .............................. 260/619 A; 260/623 R
[58] Field of Search ........... 260/623 H, 619 R, 619 A

[56] References Cited

U.S. PATENT DOCUMENTS

| | | | |
|---|---|---|---|
| 3,038,882 | 6/1962 | Gavlin | 260/623 H |
| 3,546,302 | 12/1970 | Asadorian | 260/619 R |

*Primary Examiner*—James O. Thomas, Jr.
*Assistant Examiner*—W. B. Lone
*Attorney, Agent, or Firm*—Anthony J. DeLaurentis

[57] ABSTRACT

In producing successive batches of halogenated 2,2-bis-(4-hydroxyphenyl)-propane by reacting bisphenol A with elemental halogen in acetic acid wherein the mother liquor of a preceding batch is used as the reaction medium, the improvement comprising adding to the mother liquor an acetate such as sodium acetate to react with free hydrogen halide in the reaction medium and to increase the yield.

4 Claims, No Drawings

PROCESS FOR PRODUCING HALOGENATED 2,2-BIS-(4-HYDROXYPHENYL)-PROPANE

The present invention relates to an improved process for the production of halogenated 2,2-bis-(4-hydroxyphenyl)-propane.

Halogen derivatives of the 2,2-bis-(4-hydroxyphenyl)-propane (bisphenol A), especially the tetrachloro and tetrabromo derivatives are used in the plastic industry as fire retardant components. These derivatives are fire retardant components used to obtain self-extinguishing epoxy resins, polyesters and polycarbonates.

For the manufacture of the halogenated bisphenols by chlorination or bromination of bisphenol A, processes have been known which differ in the main as a result of the solvents used during halogenation. Thus, for example, in the case of various bromination processes, mixtures of water and low aliphatic alcohols, especially methanol are described as solvents used as the reaction media. These processes have the disadvantages that beside the tetrabromobisphenol A and the di and tribromo derivates of the bisphenol A striven for; tribromophenol, and above all fairly large quantities of highly toxic methyl bromide, are obtained as a result of dissociation.

The processes described in German Pat. Nos. 1,262,283 and 1,266,309 avoid these disadvantages, because the chlorination or bromination of bisphenol A are accomplished in mixtures of benzene respectively toluene and water or of alkyl bromides and water. Toxic by-products develop but the obtaining of the simultaneously formed hydrogen halide is made difficult, since a large part of it dissolves in the water portion of the solvent and can be recovered from this only partially.

This difficulty can be successfully circumvented whenever the solvent is acetic acid which has a considerably lesser solubility for hydrogen halides than pure water. In such a method of operation, the largest part of the simultaneously formed hydrogen halide is obtained in a gaseous form and the rest, which is dissolved in the reaction medium, can be easily driven out by heating to a temperature between 80° and 100°C. Thus an anhydrous hydrogen halide which has very versatile uses can be obtained as a by-product. However this process has another decisive technical disadvantage. In order to ensure the highest possible yield of brominated bisphenol A in the case of a operation on a large industrial scale, it is necessary to reuse the mother liquor after dissociation of the end product as a solvent for the next batch. In the case of bromination of bisphenol A in acetic acid, a solution of a deep blue color is formed by reuse of the mother liquor after a few batches, which leads to a discolored end product.

Thus, it would be desirable to find a process for halogenation of bisphenol A in which a multiple reuse of the mother liquor obtained will be possible without any disadvantage.

A primary object of the present invention is to obtain an improved process for the production of halogenated 2,2-bis-(4-hydroxyphenyl) -propane (bisphenol A) by the reaction of bisphenol A with elemental halogen in acetic acid, whereby the mother liquor of a preceding batch is used as the reaction medium.

The process of the invention is distinguished by the fact that after dissociation of the halogenated bisphenol A and prior to the addition of the new bisphenol A that is to be halogenated, an acetate at least partly soluble in the mother liquor is added to the mother liquor.

For this purpose all acetates are suitable which are at least partially soluble in the acetic acid containing mother liquor or reaction medium. Preferably alkaline or alkaline earth acetates, especially sodium acetate are to be used such as sodium, potassium, calcium acetates. The quantity of acetate to be added should be regulated so that the hydrogen halide remaining in the mother liquor will be fixed or reacted and not in free form. An excess of 5 to 500%, preferably of 50 to 100%, beyond the quantity of acetate needed for the conversion of the free hydrogen halide existing in the mother liquor has turned out to be favorable. Consequently, the more carefully the hydrogen halide is driven out of the mother liquor, the less can be the quantity of acetate added.

In the method according to the invention, first of all elemental halogen, preferably chlorine or bromine is introduced into a solution of bisphenol A in acetic acid for the purpose of producing halogenated bisphenol A. The hydrogen halide formed thereby is dissolved in the acetic acid until the latter is saturated. Additional quantities escape and can be collected in a receiver, for example, with water or aqueous alkaline hydroxide solution. After the addition of halogen is completed, most of the hydrogen halide dissolved in the acetic acid is driven out by an increase in the temperature as a by product.

After the reaction mixture is cooled, the precipitated halogenated bisphenol A is dissociated in a known manner, for example, by filtration. The mother liquor obtained thereby is the reaction medium for the next batch. Before the required quantity of bisphenol A is dissolved therein for the next mixture, such quantities of acetate(s), preferably sodium acetate, are added to the mother liquor so that no free hydrogen halide is present any more or detectable. Into this buffered acetic acid solution, additional bisphenol A is added and then the conversion to halogenated bisphenol A is accomplished by introduction of the elemental halogen.

According to the method of the invention, the mother liquor can serve many times as the reaction medium without any discoloration of the solution or of the end product. Moreover, it was found that the yield in the process according to the invention clearly increased as compared to the method of operation without the addition of acetate.

The invention is further illustrated by the following nonlimiting specific examples.

EXAMPLE 1 — Comparison

First Batch 91.2 g of bisphenol A are dissolved in 500 ml of acetic acid in a reaction vessel and 269 g of bromine are slowly introduced while stirring at ambient temperature into this solution. After the addition of bromine has been completed the stirring at ambient temperature is continued for another two hours for the purpose of an after reaction. The hydrogen bromide liberated from the reaction mixture during the conversion is collected by absorption in water. After reaction has been completed, more hydrogen bromide which is still dissolved in the reaction mixture is driven out by heating the reaction mixture to a temperature of 90° C. After that, the reaction mixture is again cooled down to ambient temperature and the tetrabromobisphenol A, suspended therein, is filtered off. After washing of the filter residue with acetic acid and water and after drying, a yield of 143 g of tetrabromobisphenol A is obtained which corresponds to 65.8% of the theory. The product has a melting point of 179° to 180° C.

Second Batch

Again 91.2 g of bisphenol A are dissolved in the mother liquor. Even after a short time, this solution is colored a deep violet. Nevertheless, the operation is continued as described above and tetrabromobisphenol A is precipitated through introduction of bromine. The yield amounts to 170 g, which corresponds to 78.2% of the theory. The product has a yellowish coloring and a melting point of 179° to 181° C.

EXAMPLE 2

The mother liquor obtained in a parallel experiment to the first described method used to produce the first batch of Example 1 is mixed with 30 g of sodium acetate. Then, as described before, in a second batch operation, 91.2 g of bisphenol A are dissolved in this mother liquor and tetrabromobisphenol A precipitated under the same operating conditions as in Example 1. 211 g of colorless tetrabromobisphenol A are obtained as an end product from a solution which was not discolored. This corresponds to a yield of 97.0% of the theory versus a yield of only 78.2% in Example 1. The product has a melting point of 180° to 182° C.

What is claimed is:

1. In a process for the production of chlorinated or brominated 2,2-bis-(4-hydroxyphenyl)-propane by conversion of 2,2-bis-(4-hydroxyphenyl)-propane with elemental chlorine or bromine in individual, successive batches at a reaction temperature of from room temperature up to about 90° C. and in an acetic acid reaction medium, wherein hydrogen chloride or hydrogen bromide is formed along with the chlorinated or brominated 2,2-bis-(4-hydroxyphenyl)-propane in each successive batch reaction, and wherein the acetic acid reaction medium is the mother liquor of a preceding batch reaction, the improvement which comprises:

cooling the mother liquor of a preceding batch reaction to room temperature and separating therefrom the chlorinated or brominated 2,2-bis-(4-hydroxyphenyl)-propane formed during the reaction;

adding to said mother liquor an alkaline or alkaline earth acetate in an amount of from 5 to 500% in excess of the amount necessary for the conversion of all free hydrogen halides present in said mother liquor; and employing said mother liquor as the reaction medium in a new batch.

2. In a process according to claim 1, wherein said alkaline or alkaline earth acetate is sodium acetate.

3. In a process according to claim 1, wherein said acetate is added in an amount of from 50 to 100% in excess of the amount necessary for the conversion of all free hydrogen halides present in said mother liquor.

4. In a process according to claim 1, wherein said acetate is sodium acetate, and wherein said sodium acetate is added in an amount of from 50–100% in excess of the amount necessary for the conversion of all free hydrogen halide present in said mother liquor.

* * * * *